(12) United States Patent
Ritzenhoff et al.

(10) Patent No.: US 8,807,399 B2
(45) Date of Patent: Aug. 19, 2014

(54) DISPENSER

(75) Inventors: Andreas Franz Christian Ritzenhoff, Marburg (DE); Joerg Stock, Amoeneburg (DE); Oliver Arnold, Dautphetal-Allendorf (DE); Charles Neuner, Amityville, NY (US); Manfred Bodenbender, Kirchhain-Grossseelheim (DE)

(73) Assignee: AVENIDA GmbH & Co. KG, Marburg (DE)

( * ) Notice: Subject to any disclaimer, the term of this patent is extended or adjusted under 35 U.S.C. 154(b) by 0 days.

(21) Appl. No.: 13/453,458

(22) Filed: Apr. 23, 2012

(65) Prior Publication Data

US 2013/0082071 A1    Apr. 4, 2013

(30) Foreign Application Priority Data

Sep. 30, 2011  (DE) .......................... 10 2011 114 568
Oct. 18, 2011  (DE) .......................... 10 2011 116 054
Dec. 22, 2011  (EP) .................... PCT/EP2011/073811

(51) Int. Cl.
| | |
|---|---|
| *G01F 11/02* | (2006.01) |
| *A61M 5/315* | (2006.01) |
| *B05B 11/00* | (2006.01) |
| *A61M 5/19* | (2006.01) |

(52) U.S. Cl.
CPC ......... B05B 11/3083 (2013.01); B05B 11/3084 (2013.01); *A61M 5/19* (2013.01); B05B 11/3095 (2013.01); *A61M 5/31553* (2013.01)
USPC .......................................... 222/309; 604/211

(58) Field of Classification Search
CPC .................... B05B 11/3008; A45D 2200/056; G01F 11/023
USPC ........... 222/137, 256, 145.5, 309, 310, 144.5, 222/134, 311, 249–250, 135, 325–327, 222/386; 401/176, 143; 604/191
See application file for complete search history.

(56) References Cited

U.S. PATENT DOCUMENTS

| | | | | |
|---|---|---|---|---|
| 5,240,146 A | * | 8/1993 | Smedley et al. | ............... 222/137 |
| 5,279,586 A | * | 1/1994 | Balkwill | ........................ 604/207 |
| 5,423,752 A | * | 6/1995 | Haber et al. | .................... 604/86 |
| 5,584,815 A | * | 12/1996 | Pawelka et al. | ............... 604/191 |

(Continued)

FOREIGN PATENT DOCUMENTS

| | | |
|---|---|---|
| DE | 3744584 A1 | 7/1989 |
| DE | 10 2007 054 019 A1 | 5/2009 |

(Continued)

OTHER PUBLICATIONS

Random House Webster'S College Dictionary 452 (1991).

*Primary Examiner* — Paul R Durand
*Assistant Examiner* — Charles P Cheyney
(74) *Attorney, Agent, or Firm* — Griffin & Szipl, P.C.

(57) ABSTRACT

The present invention relates to a dispenser having an actuation device (24) for dispensing components from an output device that is connected to reservoirs (26, 27), wherein the actuation device acts on the pumping devices (34, 35) indirectly via a dosing device, and the dosing device is equipped with a setting device (23) that can be actuated to change the position of a transmission element (40) acting on the pumping devices for setting the quantity ratio, wherein both the setting device and the actuation device can be rotated about a longitudinal axis of the dispenser.

24 Claims, 10 Drawing Sheets

(56) References Cited

U.S. PATENT DOCUMENTS

| | | | |
|---|---|---|---|
| 6,164,498 A * | 12/2000 | Faughey et al. | 222/309 |
| 6,464,107 B1 | 10/2002 | Brugger | |
| 6,682,243 B2 * | 1/2004 | Iwamoto et al. | 401/75 |
| 2005/0260025 A1 * | 11/2005 | Kurihara et al. | 401/68 |
| 2009/0074500 A1 * | 3/2009 | Pires et al. | 401/31 |
| 2009/0317167 A1 * | 12/2009 | Pires et al. | 401/65 |
| 2013/0056494 A1 * | 3/2013 | Pires et al. | 222/137 |

FOREIGN PATENT DOCUMENTS

| | | |
|---|---|---|
| DE | 20 2009 014 316 U1 | 1/2011 |
| EP | 1 104 336 | 6/2001 |
| WO | 99/55468 | 11/1999 |
| WO | 00/09270 | 2/2000 |
| WO | 2011/047882 A1 | 4/2011 |

\* cited by examiner

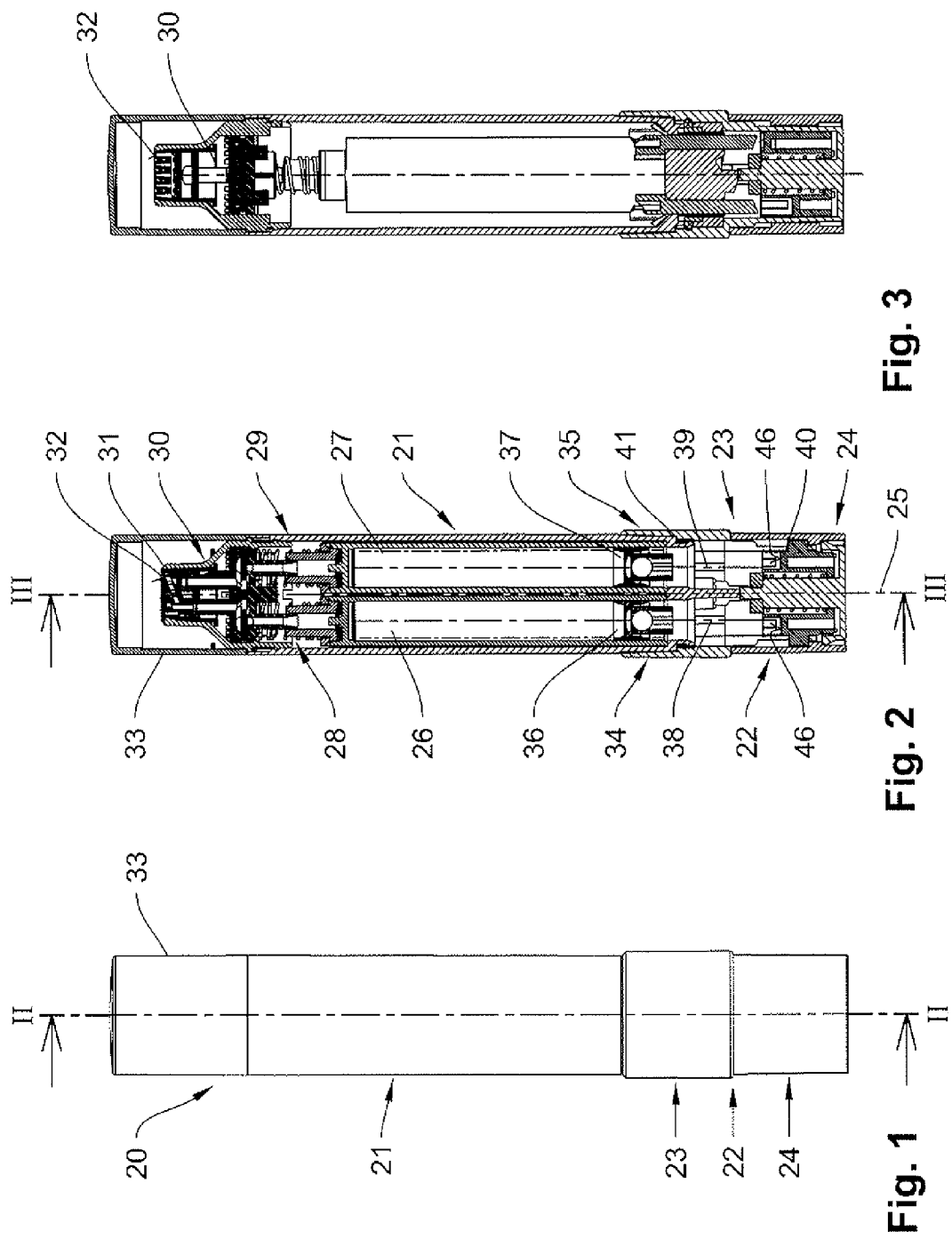

Fig. 12
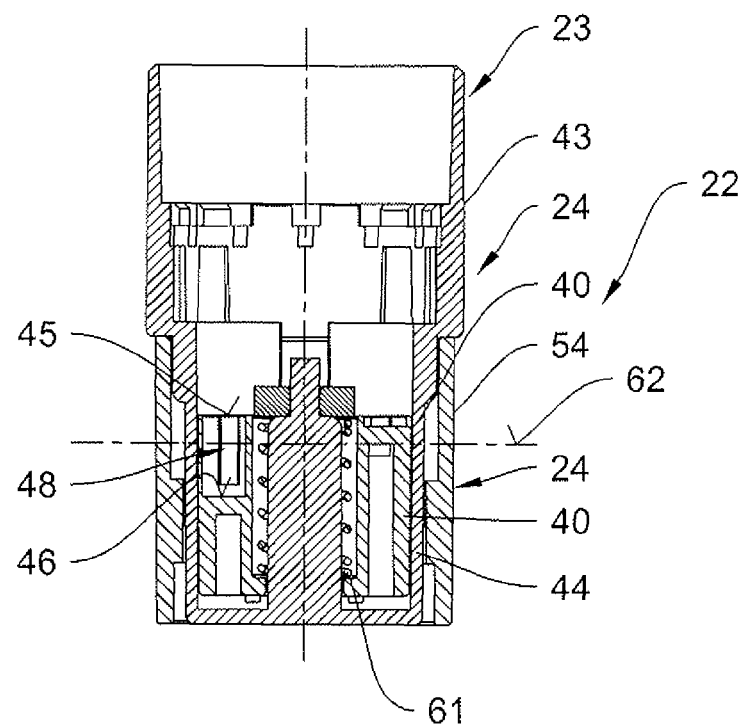
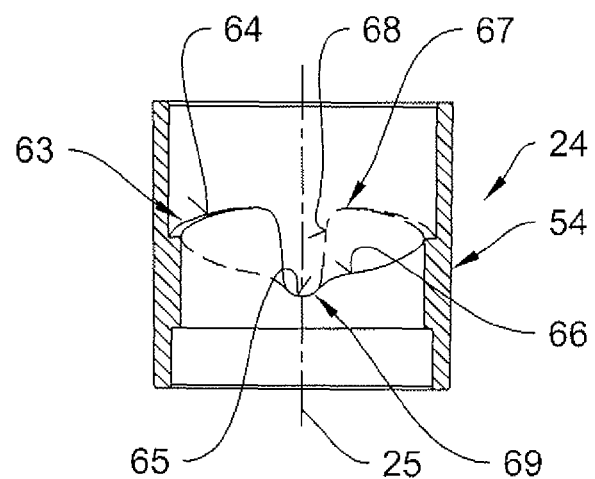
Fig. 13

Fig. 14
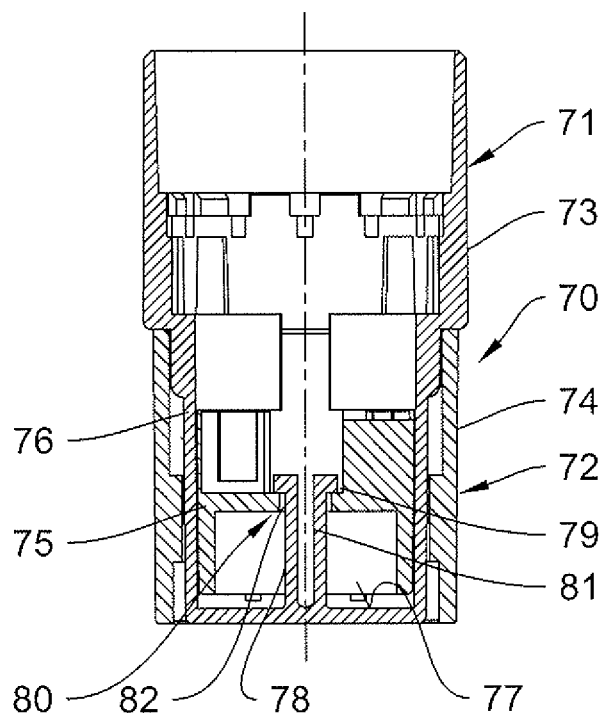
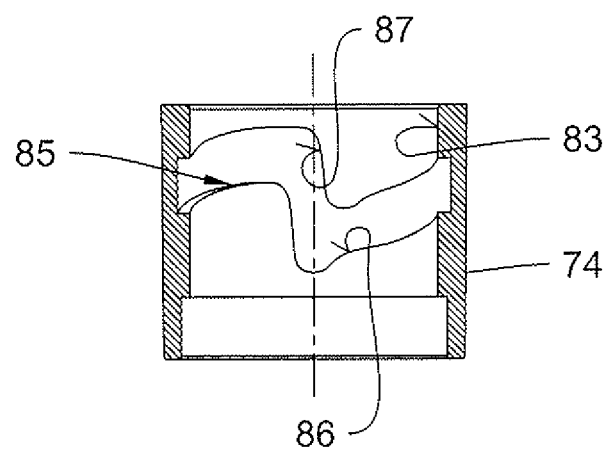
Fig. 15

Fig. 20
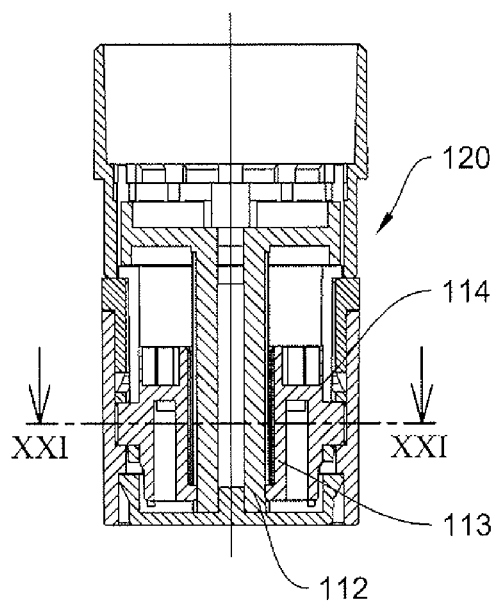
Fig. 22
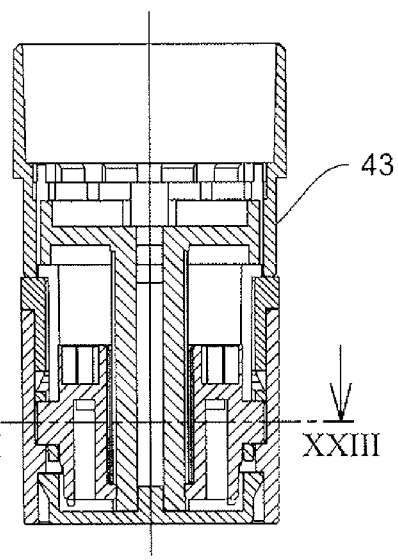
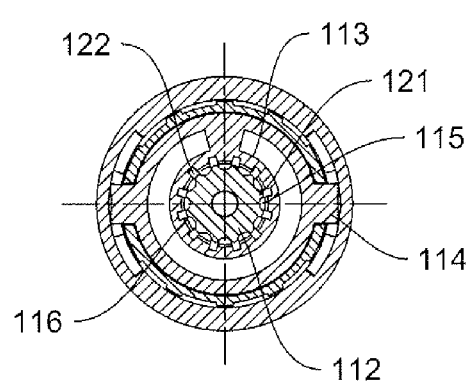
Fig. 21
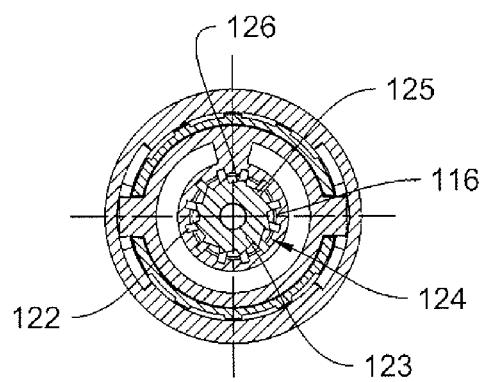
Fig. 23

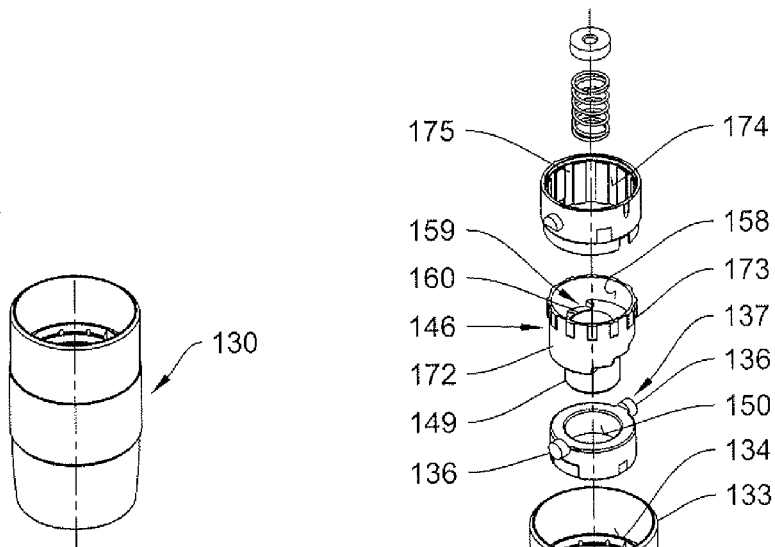
Fig. 24
Fig. 25
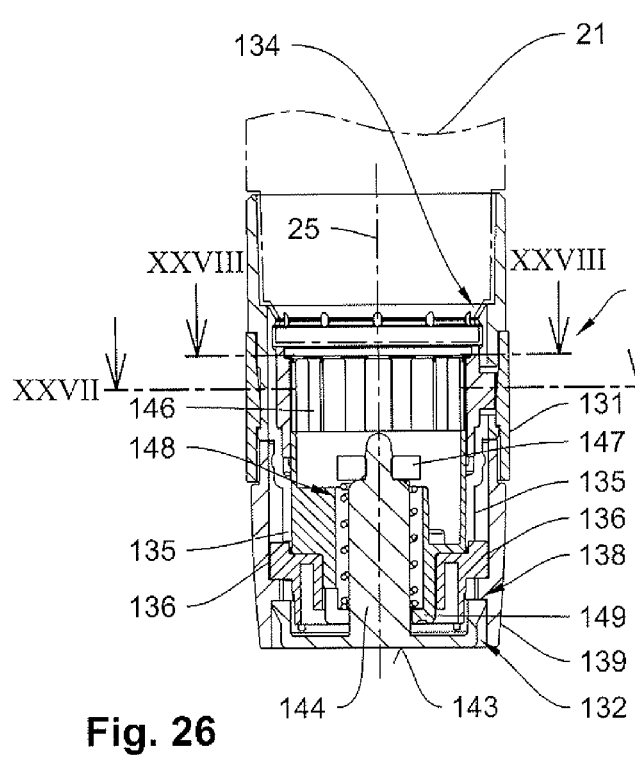
Fig. 26

Fig. 27
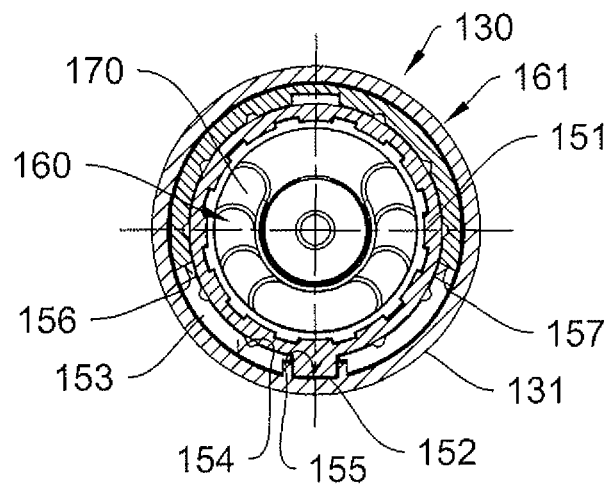
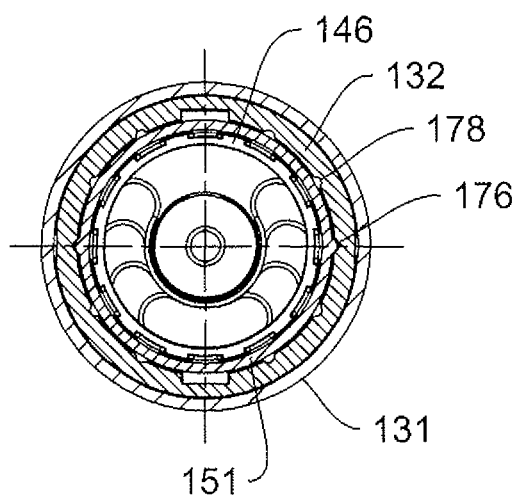
Fig. 28

US 8,807,399 B2

DISPENSER

This application claims priority from German Patent Application No. 10 2011 114 568.4, filed Sep. 30, 2011, and on German Patent Application No. 10 2011 116 054.3, filed Oct. 18, 2011, and on International Patent Application No. PCT/EP2011/073811, filed Dec. 22, 2011, the entire disclosures of which are incorporated herein by reference.

FIELD OF THE INVENTION

The present invention relates to a dispenser for the dosed dispensing of at least two components received in a reservoir, wherein each reservoir is assigned a separate pumping device and the pumping devices are equipped with an actuation device for dispensing the components from an output device connected to the reservoirs, wherein the actuation device acts on the pumping devices indirectly via a dosing device, and the dosing device is equipped with a setting device that can be actuated to change the position of a transmission element acting on the pumping devices for setting the quantity ratio of the components.

BACKGROUND OF THE INVENTION

Document EP 1 104 336 A1 discloses a dispenser of the type specified above, which has a setting device for setting the quantity ratio of the components, a transmission element that can be swiveled about a swivel axis and that acts on the pumping devices upon execution of a swivel movement. For the purpose of setting the dosing device, the swivel axis of the transmission element is rotated about the longitudinal axis of the dispenser by means of a setting device. Subsequent to setting the dosing device, an actuation force is exerted on an actuation section of the transmission element for dispensing the components from the reservoir, such that the transmission element is swiveled about the swivel axis, which runs transversely to the longitudinal axis of the dispenser, in response to the exertion of the actuation force.

One of the disadvantages of the known dispenser is that the translational actuation is necessary in the known dispenser for the purpose of executing a swivel movement of the transmission element about its swivel axis that is transversely oriented to the longitudinal axis, which, in practical applications permits only a very inaccurate dosing of the total quantity of the two components dispensed from the output device. Moreover, the output of a reproducible dispensing quantity of the two components using the known actuation devices is only possible when the transmission element executes a full cycle about the swivel axis. By contrast, the output of only a partial quantity of the possible maximum quantity is hardly possible in a reproducible manner, since the reproducible output of a partial quantity requires a correspondingly reproducible execution of a partial cycle of the transmission element. However, the execution of a defined cycle of the transmission element is scarcely possible in the light of the overall very short distance traveled by the transmission element when a swivel movement is executed.

Thus, it is an object of the present invention to provide a dispenser that enables an accurate dosing of a dispensing quantity composed of two components. Moreover, it is an object of the invention to provide a dispenser that can be operated in a simple manner and, thus, provides a higher level of operating convenience on the part of the user.

SUMMARY OF THE INVENTION

To achieve this object, the inventive dispenser exhibits the features of a first embodiment of the present invention, which pertains to a dispenser (20, 88, 110) for the for dosed dispensing of at least two components received in a reservoir (26, 27), wherein each reservoir (26, 27) is assigned a separate pumping device (34, 35) and the pumping devices are equipped with an actuation device (24, 72, 90, 162) for dispensing the components from an output device (31) connected to the reservoirs (26, 27), wherein the actuation device (24, 72, 90, 162) acts on the pumping devices (34, 35) indirectly via a dosing device and the dosing device is equipped with a setting device (23, 71, 89, 161), which can be actuated to change the position of a transmission element (40, 75, 114, 146) acting on the pumping devices (34, 35) for setting the quantity ratio of the components, characterized in that both the setting device (23, 71, 89, 161) for setting the quantity ratio of the components and the actuation device (24, 72, 90, 162) for dispensing the components from the output device (31), for the purpose of actuation, can be rotated about a longitudinal axis (25) of the dispenser (20, 88, 110). In accordance with a second embodiment of the present invention, the first embodiment is modified so that the setting device (23, 71, 89, 161) of the dosing device has an adjusting housing (43, 73, 92, 131) that can be rotated about the longitudinal axis (25) of a reservoir housing (21), in which the reservoirs (26, 27) for receiving the components and the pumping devices (34, 35) are received, and in which the transmission element (40, 75, 114, 146) is disposed so as to be rotationally fixed with respect to the adjusting housing (43, 73, 92, 131) and so as to be axially displaceable on the longitudinal axis of the adjusting housing for actuating the pumping device (34, 35), wherein the transmission element features a contact surface (45, 159) of an annular design or is formed as a ring segment that has a surface contour changing in shape along its circumference and interacting with the pumping pistons (36, 37) of the pumping devices (34, 35).

In accordance with a third embodiment of the present invention, the second embodiment is further modified so that the actuation device (24, 72, 90, 162) for dispensing the components has an actuating housing (54, 74, 93, 139), which can be rotated about the longitudinal axis (25) of the dispenser (20) relative to the adjusting housing (43, 73, 92, 131), and the actuating housing is equipped with a guide arrangement to enable the axial displacement of the transmission element (40, 75, 114, 146), wherein a first guide device of the guide arrangement, which is formed in the actuating housing (54, 75, 93, 139), interacts with a second guide device of the guide arrangement, which is formed independently of the actuating housing, for converting a rotary movement of the actuating housing into an axial movement of the transmission element. In accordance with a fourth embodiment of the present invention, the third embodiment is further modified so that the second guide device has a guide section (44, 76, 94, 132) having an axially oriented guide slot (50, 95, 135) and a pin arrangement positioned at the transmission element (40, 75, 114, 146) with at least one radial guide pin (49, 136) that penetrates through the guide slot, and with its contact end interacts with the first guide device of the actuating housing (54, 74, 93, 139).

In accordance with a fifth embodiment of the present invention, the third embodiment or the fourth embodiment are further modified so that the actuating housing (54, 74, 93, 139), for the purpose of forming the first guide device, on its inner wall (51, 83, 140), is coaxially disposed with respect to the guide section (44, 76, 94, 132) that has a guide path having a contact contour (64, 142) interacting with the contact end of the guide pin (49, 136) and that controls the axial movement of the transmission element (40, 75, 114, 146). In accordance with a sixth embodiment of the present invention, the fourth embodiment or the fifth embodiment are further modified so that the axially oriented guide slot (95, 135) formed in the guide section (94, 132) at its lower end features a pin catch (96) for accommodating the radial guide pin (49, 136) to define a direction of rotation of the actuation device (90, 162). In accordance with a seventh embodiment of the present invention, the first embodiment, the second embodiment, the third embodiment, the fourth embodiment, the fifth embodiment and the sixth embodiment, are further modified so that, for the purpose of defining an initial position of the actuation device (24, 162), in which the pumping devices (34, 35) are not acted upon by the transmission element (40, 146), a spring device is disposed between a stop (59, 147) formed at the guide section (44) and the transmission element (40, 146). In accordance with an eighth embodiment of the present invention, the seventh embodiment is further modified so that the stop (59, 147) is formed at the axial end of a pin (58, 144) formed at the bottom of the guide section (44, 132) and extending through an opening formed in a bottom (60, 143) of a central cup-shaped indentation of the transmission element (40, 146), wherein the spring device is configured in the form of a helical spring (61, 148), which is disposed in an annular space formed between the pin and the indentation and which extends between the stop and the bottom.

In accordance with a ninth embodiment of the present invention, the first embodiment, the second embodiment, the third embodiment, the fourth embodiment, the fifth embodiment and the sixth embodiment, are further modified so that, for the purpose of defining an initial position of the actuation device (72), in which the pumping devices are not acted upon by the transmission element (75), a latching device (80) is disposed at an axial end of a latching pin (78), which is arranged in the guide section (76), and in which the transmission element (75) is disposed in the initial position, engages behind an edge of a central opening (82) in the transmission element (75). In accordance with a tenth embodiment of the present invention, the first embodiment, the second embodiment, the third embodiment, the fourth embodiment, the fifth embodiment, the sixth embodiment, the seventh embodiment, the eighth embodiment, and the ninth embodiment, are further modified so that the guide path disposed in the inner wall (83) of the actuating housing (74) is designed in the form of a guide groove (85), wherein the groove edges (86, 87) thereof, which run in parallel to one another, receive the guide pin (49) between them. In accordance with an eleventh embodiment of the present invention, the first embodiment, the second embodiment, the third embodiment, the fourth embodiment, the fifth embodiment, the sixth embodiment, the seventh embodiment, the eighth embodiment, the ninth embodiment, and the tenth embodiment, are further modified so that, for forming the second guide device, the guide section (44, 76, 94) is formed by the adjusting housing (43, 73, 92) and the pin arrangement with the at least one guide pin (49) is formed at the transmission element (40, 75, 114, 146) so that when the adjusting housing is rotated the transmission element is correspondingly rotated as well.

In accordance with a twelfth embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, and the eleventh embodiment, are further modified so that, for the purpose of the defined relative arrangement of the adjusting housing (43, 73, 92) with respect to the reservoir housing (21), a latching device (41, 97, 111) is formed between the adjusting housing (43, 73, 92) and the reservoir housing (21) and has a plurality of indexed positions for a defined assignment of contact regions of the transmission element (40, 75, 114) that is formed on the contact surface (45), and plungers (38, 39) act on the pumping pistons (36, 37) of the pumping devices (34, 35). In accordance with a thirteenth embodiment of the present invention, the twelfth embodiment is further modified so that the latching device (97) is formed as a modular latching unit that can be inserted between the reservoir housing (21) and the adjusting housing (92), and which can be actuated as a function of the direction of rotation with respect to the reservoir housing to enable the relative rotation of the adjusting housing.

In accordance with a fourteenth embodiment of the present invention, the thirteenth embodiment is further modified so that the latching unit features a first latching element (98) of an annular design, which can be connected to the reservoir housing (21) in a rotationally fixed manner, and a second latching element (99) of an annular design, which can be connected to the adjusting housing (92) in a rotationally fixed manner, wherein the latching elements interact with one another via a latching engagement that is produced in a common annular plane with the aid of latching projections, wherein the latching projections are formed by a toothed pawl section (106, 107). In accordance with a fifteenth embodiment of the present invention, the fourteenth embodiment is further modified so that one of the two latching elements (98, 99) features the toothed pawl section (106, 107) only in a ring segment. In accordance with a sixteenth embodiment of the present invention, the twelfth embodiment is further modified so that the latching device (11) features a latching axle (112) that is connected to the reservoir housing (21) and that engages with a hub of the transmission element (114) that is designed as a latching sleeve (113) to produce a latching engagement. In accordance with a seventeenth embodiment of the present invention, the sixteenth embodiment is further modified so that latching projections formed on the circumference of the latching axle (112) interact with latching projections that are formed on the bore wall of the latching sleeve (113) to produce the latching engagement. In accordance with an eighteenth embodiment of the present invention, the seventeenth embodiment is further modified so that the latching projections are formed by a toothed latching portion (124).

In accordance with a nineteenth embodiment of the present invention, the first embodiment, the second embodiment, the third embodiment, the fourth embodiment, the fifth embodiment, the sixth embodiment, the seventh embodiment, the eighth embodiment, the ninth embodiment, and the tenth embodiment, are further modified so that, for forming the second guide device, the guide section is connected to the reservoir housing (21) in a rotationally fixed manner, wherein the pin arrangement is formed as a guide ring (137) having at least one guide pin (136) and the transmission element (146) is received in the guide ring so as to be rotatable and is connected to the adjusting housing (131) in a rotationally fixed manner by means of a radial engagement device, such that when the adjusting housing is rotated, a relative rotation with respect to the guide housing is effected by the same as well. In accordance with a twentieth embodiment of the present invention, the nineteenth embodiment is further modified so that the engagement device features a setting sleeve (151) in which the transmission element (146) is received in a rotationally fixed manner and so as to be axially displaceable, wherein the setting sleeve produces an engaging connection with the adjusting housing (131) via a setting pin (152), which penetrates radially through the guide section in a setting groove (153). In accordance with a twenty-first embodiment of the present invention, the twentieth embodiment is further modified so that, for the purpose of the defined relative arrangement of the adjusting housing (131), a latching device is formed between the setting sleeve (151) and the guide section (132) and has a plurality of indexed positions for a defined assignment of contact regions of the transmission element (146) formed on the contact surface (159), and plungers (38, 39) act on the pumping devices (34, 35).

In accordance with a twenty-second embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, the fifteenth embodiment, the sixteenth embodiment, the seventeenth embodiment, the eighteenth embodiment, the nineteenth embodiment, the twentieth embodiment and the twenty-first embodiment, are further modified so that the contact regions are formed on the contact surface (45, 159) of the transmission element (40, 75, 146) by contact ledges (46, 170) that are arranged in a stepped sequence. In accordance with a twenty-third embodiment of the present invention, the twenty-second embodiment is further modified so that the contact ledges (46) are formed by blind bores (48) that are arranged in a horizontal surface of the transmission element (40, 75).

In the inventive dispenser, both the setting devices for setting the quantity ratio of the components and the actuation device for dispensing the components from the output device, for the purpose of actuation, can be rotated about a longitudinal axis of the dispenser. According to the invention, use is made of the aspect that the user of a dispenser basically perceives it more convenient to execute the actuations or the settings, which are to be performed by the user at the dispenser, by carrying out similar manual movements. The reason can be seen, in particular, in the light of the aspect that in the inventive dispenser, the manipulation of the dispenser is not required to be altered between the setting of the mixing ratio of the components and the actuation for dispensing of the components in the set mixing ratio. Instead, in both cases, a rotational movement about the longitudinal axis of the dispenser needs to be executed. Moreover, the invention is based on the aspect that, for ergonomic reasons, it is much easier for the user of such a dispenser to execute a reproducible rotational movement than it is to execute a translational movement, in particular, in any instance where the travel path available for effecting the translational movement is rather short.

In a preferred embodiment of the dispenser, the setting device of the dosing device has an adjusting housing that can be rotated about the longitudinal axis of a reservoir housing, in which the reservoirs for receiving the components and the pumping devices are received, and in which the transmission element is disposed therein so as to be rotationally fixed with respect to the adjusting housing and so as to be axially displaceable on the longitudinal axis of the adjusting housing for actuating the pumping devices, wherein the transmission element features a contact surface of an annular design, or is formed as a ring segment, which has a surface contour changing in shape along its circumference and interacting with the pumping devices. In this advantageous embodiment, the special design of the setting device thus makes it possible to convert a manual rotational movement of the adjusting housing, caused by the user acting upon the adjusting housing from the outside, into an axial or else translational movement of the transmission element, such that, on the one hand, an advantageous rotational displacement of the setting device with a view to ergonomics is enabled by the user and, on the other hand, the axial adjusting movement of the transmission element enables a functionally reliable actuation of the pumping devices, wherein the horizontal orientation of the transmission element with respect to a vertical orientation of the longitudinal axis of the dispenser is always maintained.

In particular, when the transmission element acts upon the pumping devices, relative movements between the transmission element and the pumping devices are not produced, which may give rise to wear and tear, potentially preventing a reliable and desirably durable, as well as secure, use of the dispenser. The setting of the desired quantity ratio between the two components provided for the dispensing is performed by merely rotating the transmission element about the longitudinal axis of the dispenser and the adjusting housing until the relative position of the transmission element, with respect to the pumping devices, is reached, in which the different contact regions of the transmission element defining the quantity ratio are assigned to the pumping devices.

Advantageously, the actuation device can have an actuating housing that can be rotated about the longitudinal axis of the dispenser relative to the adjusting housing for dispensing the components, wherein the actuating housing is equipped with a guide arrangement to enable the axial displacement of the transmission element, wherein a first guide device of the guide arrangement, which is formed in the actuating housing, interacts with a second guide device of the guide arrangement, which is formed independently of the actuating housing, for converting a rotary movement of the actuating housing into an axial movement of the transmission element. A particularly functionally reliable and, at the same time easily implementable, design of the second guide device is enabled if the second guide device has a guide section having an axially oriented guide slot and a pin arrangement positioned at the transmission element with at least one radial guide pin, which penetrates through the guide slot and with its contact end interacts with the first guide device of the actuating housing.

It is equally particularly advantageous if the actuating housing, for the purpose of forming the guide device, on its inner wall is coaxially disposed with respect to the guide section of the adjusting housing that has a guide path having a contact contour interacting with the contact end of the guide pin and controlling the axial movement of the transmission element, such that the coaxial arrangement of the actuating housing with respect to the adjusting housing enables an overall compact design of the dispenser. A detent for the direction of rotation, or a definition of a possible direction of rotation, can be realized if the axially oriented guide slot formed in the guide section, at its lower end, features a pin catch for accommodating the radial guide pin in order to define a direction of rotation of the actuation device.

A particularly advantageous embodiment of the dispenser, which contributes to further enhancing the reproducibility of defined dispensing quantities of the dispenser, for the purpose of defining an initial position of the actuation device, in which the pumping devices are not acted upon by the transmission element, includes a spring device disposed between a stop formed at the guide section and the transmission element, such that the initial position can be accurately detected by the user with a view to haptics and resistance against the rotational displacement of the actuation device is minimized. It is particularly advantageous if the stop is formed at the axial end of a pin formed at the bottom of the guide section and is extending through an opening formed in a bottom of a central cup-shaped indentation of the transmission element, and if the spring device is configured in the form of a helical spring that is disposed in an annular space formed between the pin and the indentation and that extends between the stop and the bottom. By means of this measure, a secure housing for the spring device is created such that the function of the spring device is ensured even over a long period of use of the dispenser.

Alternatively to the design of the dispenser with a spring device, for defining an initial position of the actuation device, it is also advantageously possible to make provision for a latching device that is disposed at an axial end of a latching pin, which is arranged in the guide section, and which in the transmission element is disposed in the initial position, and that engages behind an edge of a central opening in the transmission element. In this embodiment of the dispenser, wherein the constructional measures for defining the initial position of the actuation device are carried out in a particularly simple manner, it proves to be advantageous to ensure a reliable functioning if the guide path disposed in the inner wall of the actuating housing is designed in the form of a guide groove, wherein the groove edges thereof run in parallel to one another and receive the guide pin between them.

It is equally advantageous if, for forming the second guide device, the guide section is formed by the adjusting housing and the pin arrangement with the at least one guide pin is formed at the transmission element, such that when the adjusting housing is rotated, the transmission element is correspondingly rotated as well. In this way, the adjusting housing performs an advantageous double function, such that it is possible to correspondingly reduce the number of individual parts.

In a particularly advantageous embodiment of the dispenser, for purpose of the defined relative arrangement of the adjusting housing with respect to the reservoir housing, a latching device is formed between the adjusting housing and the reservoir housing and has a plurality of indexed positions for a defined assignment of contact regions of the transmission element formed on the contact surface, and plungers act on the pumping pistons of the pumping devices. On the one hand, the latching device facilitates the repeated setting of a relative rotational position between the adjusting housing and the reservoir housing for the purpose of reproducibly setting a mixing ratio. On the other hand, the setting of a once set mixing ratio between the components can also be secured by the latching device. If the latching device is formed as a modular latching unit that can be inserted between the reservoir housing and the adjusting housing and that can be actuated as a function of the direction of rotation with respect to the reservoir housing to enable the relative rotation of the adjusting housing, it is possible to set the direction of rotation by simply exchanging the latching device.

It is particularly advantageous if the latching unit features a first latching element of an annular design, which can be connected to the reservoir housing in a rotationally fixed manner, and a second latching element of an annular design, which can be connected to the adjusting housing in a rotationally fixed manner. In this way, latching elements interact with one another via a latching engagement, which is produced in a common annular plane with the aid of latching projections, wherein the latching projections are formed by a toothed pawl portion, such that the latching device can be realized by saving a great deal of material and space. An elastically resilient latching engagement is realized if one of the two latching elements has the toothed pawl portion only in a ring segment.

A particularly accurate relative alignment between the reservoir housing and the adjusting housing is enabled if the latching device features a latching axle, which is connected to the reservoir housing and which engages with a hub of the transmission element, that is designed as a latching sleeve to produce a latching engagement. It is advantageous if the latching projections formed on the circumference of the latching axle interact with latching projections formed on the bore wall of the sleeve to produce the latching engagement. A particularly functionally reliable design can be realized if the latching projections are formed by a toothed pawl portion.

In an advantageous embodiment for forming the second guide device, the guide section is connected to the reservoir housing in a rotationally fixed manner, and the pin arrangement is designed as a guide ring having at least one guide pin. Beyond that, the transmission element is received in the guide ring so as to be rotatable and is connected to the adjusting housing in a rotationally fixed manner by means of a radial engagement device, such that when the adjusting housing is rotated, a relative rotation with respect to the guide housing is effected by the same. In this way, it can be prevented that the plungers are acted upon by a torque when a force is exerted on the plungers of the pumping devices.

If the engagement device features a setting sleeve in which the transmission element is received in a rotationally fixed manner and so as to be axially displaceable, wherein the setting sleeve produces an engaging connection with the adjusting housing via a setting pin that penetrates radially through the guide section in a setting groove, the adjusting housing can be formed as an adjusting ring. If, for the purpose of the defined relative arrangement of the adjusting housing, a latching device is formed between the setting sleeve and the guide section and has a plurality of indexed positions for a defined assignment of contact regions of the transmission element that are formed on the contact surface, and plungers act on the pumping devices, in spite of a possible simple configuration of the adjusting housing in the form of a ring, a reproducible setting is enabled. If, according to a particularly advantageous embodiment, the contact regions are formed on the contact surface of the transmission element by contact ledges that are arranged in a stepped sequence, irrespective of the surface contour and topography changing along the circumference of the transmission element, it is ensured that identical contact conditions are always created between the transmission element and the plunger independently of the relative position of the transmission element with respect to the plungers. Moreover, if the contact ledges are formed by blind bores that are arranged in a horizontal surface of the transmission element, a particularly accurate adaptation between the contact regions and the plungers of the pumping devices is enabled, such that otherwise potentially occurring wear and tear can be avoided.

BRIEF DESCRIPTION OF THE DRAWINGS

Advantageous embodiments of the dispenser will be described hereinafter in more detail with reference to the drawings.

In the drawings:

FIG. 1: illustrates an embodiment, according to the present invention, of a dispenser having a reservoir housing with a manipulation device;

FIG. 2: illustrates the dispenser shown in FIG. 1 in a cross-sectional view according to intersection lines II-II of FIG. 1;

FIG. 3: illustrates a cross-sectional view according to intersection lines III-III of FIG. 2;

FIG. 12: illustrates a cross-sectional view of the manipulation device shown in FIG. 10 according to intersection lines XII-XII of FIG. 10;

FIG. 13: illustrates an individual view of an actuating housing coaxially connected to a guide section of the adjusting housing according to the view of FIG. 11;

FIG. 14: illustrates another embodiment of a manipulation device according to the present invention, in a view corresponding to FIG. 12;

FIG. 15 illustrates an actuating housing for combination with the adjusting housing of the manipulation device shown in FIG. 14, FIG. 16: illustrates another embodiment of a dispenser in a longitudinal cross-sectional view;

FIG. 20: illustrates a longitudinal cross-sectional view of the manipulation device shown in FIG. 19;

FIG. 21: illustrates a cross-sectional view of the manipulation device shown in FIG. 20;

FIG. 22: illustrates another embodiment of a manipulation device in a longitudinal cross-sectional view;

FIG. 23: illustrates a cross-sectional view of the manipulation device shown in FIG. 22.

FIG. 24 illustrates an isomeric view of another manipulation device;

FIG. 25 illustrates an exploded view of the manipulation device shown in FIG. 24;

FIG. 26 illustrates a cross-sectional view of the manipulation device shown in FIG. 24;

FIG. 27 illustrates a cross-sectional view of the manipulation device shown in FIG. 26 according to intersection lines XXVII-XXVII;

FIG. 28 illustrates a cross-sectional view of the manipulation device shown in FIG. 26 according to intersection lines XXVIII-XXVIII.

DETAILED DESCRIPTION OF THE INVENTION

Figure 7:
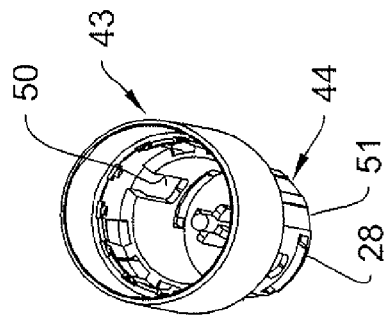
FIG. 7: illustrates an isomeric view of the adjusting housing shown in FIG. 5.

FIGS. 1, 2 and 3 provide an overall view illustrating a dispenser 20, in accordance with the present invention, which features a manipulation device 22 that is connected to a reservoir housing 21 and that combines a setting device 23 with an actuation device 24, wherein the setting device 23 and the actuation device 24 are each connected to the reservoir housing 21 relative to each other and so as to be rotatable about a longitudinal axis 25 of the dispenser 20 with respect to the reservoir housing 21. As illustrated in particular in FIGS. 2 and 3, the reservoir housing 21 essentially serves for receiving two reservoirs 26 and 27, which in the present case are designed in a cartridge-shaped manner, and each contain a component of a viscous material, which in the case of the exemplary embodiment of the dispenser illustrated here is a lip care substance furnished with pigments, which is dispensed with the aid of a valve device 28 and a mixing device 30, each assigned to one reservoir and here disposed above the reservoirs 26, 27 in the reservoir housing 21, and is finally supplied here to an applicator surface 32 via a common output device 31, from which the mixed components, which in the case of the dispenser 20 in the present case are configured as a lip cream applicator, can be applied to the lips of the user. For covering the applicator surface 32 when the dispenser 20 is not in use the reservoir housing 21 is furnished with an applicator cap 33. As is illustrated in particular in FIG. 2, pumping devices 34, 35 are disposed at the lower end of the reservoirs 26, 27, and each exerts an indirect pressure on the components received in the reservoirs 26, 27 by means of pumping pistons 36, 37, which are each acted upon by a plunger 38, 39 of a transmission element 40, which is a part of the setting device 23 of the manipulation device 22.

Figure 6:
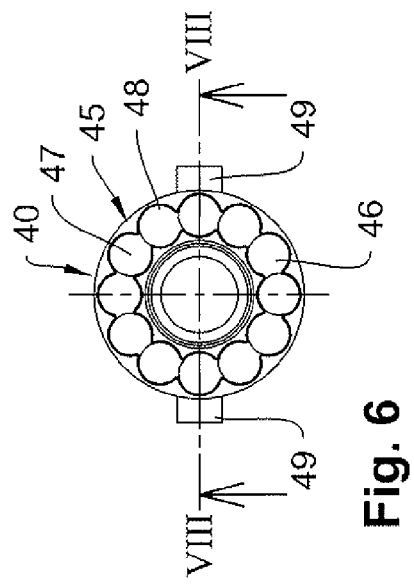
FIG. 6: illustrates a transmission element of the manipulation device shown in FIG. 5 in a top view.
Figure 5:
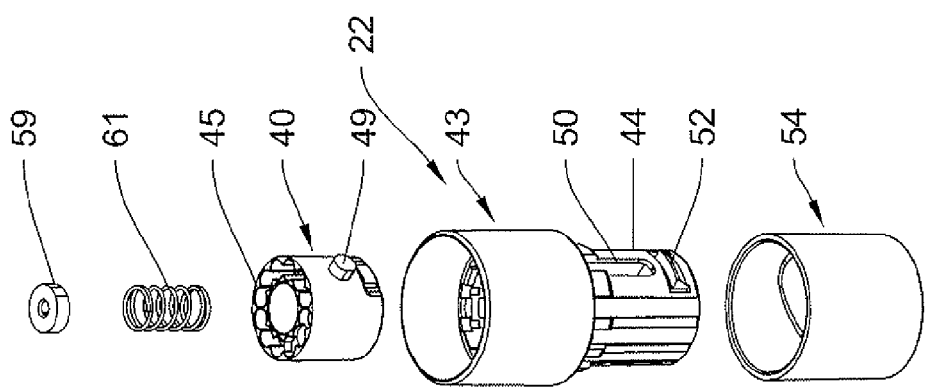
FIG. 5: illustrates an exploded view of the manipulation device shown in FIG. 4.
Figure 4:
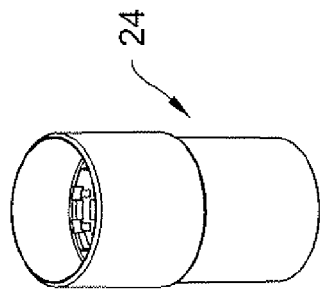
FIG. 4: illustrates the manipulation device formed of a setting device and an actuation device of the dispenser shown in FIG. 1.
Figure 8:
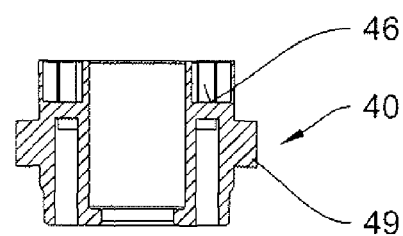
FIG. 8: illustrates a cross-sectional view of the transmission element shown in FIG. 6 corresponding to intersection lines VIII-VIII of FIG. 6.
Figure 9:
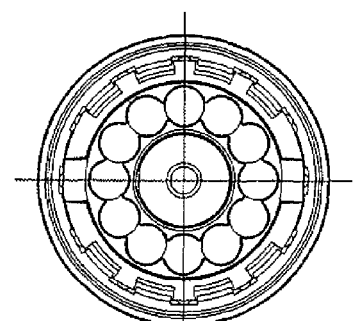
FIG. 9: illustrates a top view of the transmission element inserted into the adjusting housing.

The manipulation device 22 shown in FIG. 2 and FIGS. 4 and 5 is connected to the reservoir housing 21 via a latching connection 41 shown in FIG. 2. The setting device 23 has an adjusting housing 43, wherein the upper part thereof is formed as a guide section 44 for receiving the transmission element 40. The transmission element 40 in the present case is formed in a sleeve-like manner and has a contact surface 45 that is annularly formed at the upper axial end of the transmission element and is equipped with an annularly arranged sequence of contact ledges 46 (FIG. 6), which in the present case, are formed by bottoms 47 of blind bores 48 provided in the contact surface 45. The transmission element 40 at its outer wall features two guide pins 49 that are diametrically opposed to each other and that are each axially guided in a guide slot 50 formed in the guide section 44 of the adjusting housing 43 in the form of an oblong hole. As is apparent from a combined view of FIGS. 5, 7 and 10, the guide section 44 of the adjusting housing 43 at its lower end features a latching edge 52 adjacent to a bottom 51, which engages behind a latching web 55 formed on an inner wall 53 of an actuating housing 54 of the actuation device 24 for producing a latching connection 56 between the actuating housing 54 and the adjusting housing 43.

Figure 10:
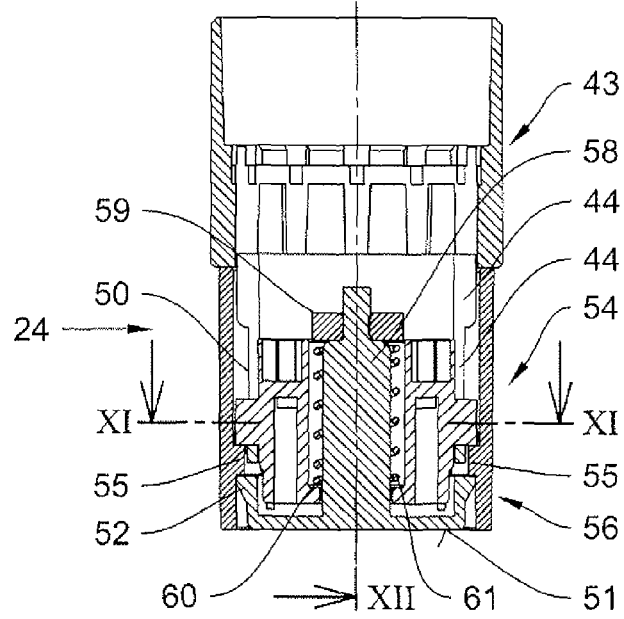
FIG. 10: illustrates a cross-sectional view of the manipulation device shown in FIG. 4 having a transmission element disposed in the initial position.
Figure 11:
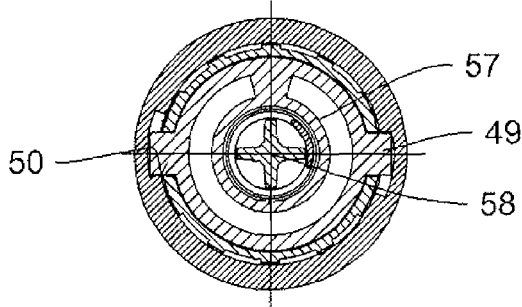
FIG. 11: illustrates a cross-sectional view of the manipulation device shown in FIG. 10 according to intersection lines XI-XI of FIG. 10.

In the latched engagement between the actuating housing 54 and the adjusting housing 43, as is in particular shown in FIGS. 10 and 11, the transmission element 40 is guided with the aid of a central bearing sleeve 57 on a pin 58 formed at the bottom 51. The pin 58, in the case of the exemplary embodiment shown in FIG. 10, at its upper end is equipped with a stop 59, here formed as an axial retaining ring, which is disposed opposite to a bottom 60 of the bearing sleeve 57 and together with the bottom respectively forms an axial support for a helical spring 61 arranged on the pin 58. The embodiment shown in FIG. 10 thus enables an axial displacement of the transmission element 40 on the pin 58 counter to the compressive force generated in this process by the helical spring 61. In this axial displacement, the transmission element 40 is guided by the guide pins 49 in the guide slots 30 of the guide section 44 of the adjusting housing 43.

As is apparent from a comparison of FIGS. 10 and 12, which illustrate different cross-sectional views of the manipulation device 22, the blind bores 48 are arranged in the contact surface 45 of the transmission element 40 for forming the contact ledges 46 and have different depths, so that the contact ledges formed by the bottoms 47 of the blind bores 48 are disposed at different levels with respect to a central contact plane 62. Differing herefrom, FIG. 12 shows contact ledges 46 that are diametrically opposed to each other at a level differing from the level of the central contact surface plane 62, so that upon axial displacement of the transmission element 40 counter to the effect of the helical spring 61, when the plungers 38, 39 are contacted with the contact ledges 46, the plungers 38, 39 are axially deflected to different extents, with the consequence that the pumping pistons 36, 37 of the pumping devices 34, 35 equally execute different strokes.

In FIGS. 10 and 12, the transmission element 40 is illustrated in different cross-sectional views of the manipulation device 22 in its initial position, in which the helical spring 61 features its maximum possible relaxation and the guide pins 49 abut against the lower stop of the guide slots 50. For the axial displacement of the transmission element 40 in the guide section 44, the actuating housing 54 of the actuation device 24, at its inner wall, is furnished with a guide path, in particular illustrated in FIG. 13, which here is formed as a guide web 63 having a contact contour 64 that abuts against the guide pins 49 of the transmission element 40 (FIG. 10), so that a relative movement of the actuating housing 54 of the actuation device 24 about the longitudinal axis 25 with respect to the adjusting housing 43 of the setting device 23 causes an axial movement of the transmission element 40 corresponding to the course of the contact contour 64.

The contact contour 64 of the guide web 63 features an indentation 65 defining the initial position of the transmission element 40 in such a manner that, corresponding to the contact contour 64 illustrated in FIG. 13, a relative movement of the actuating housing 54 about the longitudinal axis 25 in a clockwise direction causes the transmission element 40 to be axially moved upwardly along an upwards ramp 66. Upon reaching a ramp vertex 67, which is illustrated in FIG. 13 in dash-dotted lines, in response to the pretensioning force of the helical spring 61, the transmission element 40 is caused to move along an upwards ramp 68 back into a second indentation 69, which is diametrically opposed to the first indentation 65, wherein the actuating housing 54 has executed a rotation of 180° about the longitudinal axis 25. In the axial forward movement of the transmission element 40 specified above in the adjusting housing 43 of the setting device 23, the adjusting housing 43 is disposed in a defined relative arrangement with respect to the reservoir housing 21, so that the rotational position of the transmission element 40 is not changed either with respect to the plungers 38, 39.

As already specified beforehand with reference to FIG. 10, the embodiment of the transmission element shown in FIG. 2, wherein the contact ledges 46 are diametrically opposed to each other are arranged at the same level, gives rise to a correspondingly identical axial displacement of the plungers 38, 39. As a consequence, the pumping devices 34, 35 each retrieve identical quantities from the reservoirs to be fed into the mixing device 30, and to be dispensed therefrom, through the output device 31 to the applicator surface 32. For setting a different mixing ratio between the components received in the reservoirs 26, 27, the adjusting housing 43 of the setting device 23 can be rotated about the longitudinal axis 25 together with the actuating housing 54 of the actuation device 54 disposed thereon until the plungers 38, 39 are assigned axially flush contact ledges 46, which are disposed at different levels, as is, for instance, shown in FIG. 12, so that contacting of the contact ledges 46, in response to a subsequent forward movement of the transmission element against the plungers 38, 39 upon further rotation of the actuating housing 54 with respect to the adjusting housing 43, causes the plungers 38, 39 to be accordingly deflected to different extents, with the further consequence that correspondingly different quantities of the components are retrieved from the reservoirs 26, 27 to be fed into the mixing device 30 and to be dispensed therefrom to the applicator surface 32.

FIGS. 14 and 15, in another embodiment, show a manipulation device 70 that includes a setting device 71 and an actuation device 72, which have an adjusting housing 73 and an actuating housing 74 as well as a transmission element 75. Compared to the adjusting housing 43, the actuating housing 54 and the transmission element 40 of the manipulation device 22, in particular, shown in FIGS. 10 and 12, exhibit modifications that will be explained hereinafter.

For defining the initial position of the actuation device 72, a latching pin 78 is provided in a guide section 76 of the adjusting housing 73 at the bottom 77. This latching pin 78, at its axial end, features a latching device 80 formed by elastically configured latching noses 79 and engage behind an opening edge 81 of a central opening 82 in the transmission element 75.

For guiding the guide pins, which are not illustrated in greater detail in the view according to FIG. 14, but which are identical to the guide pins 49 of the transmission element 40, in an inner wall 83 of the actuating housing 74, a guide path is designed in the form of a guide groove 85 and has groove edges 86, 87 extending in parallel to each other and that receive the guide pins between them. Thus, so both in the event of an upward movement and in the event of a downward movement of the transmission element 75, a reliable positive engagement is produced between the guide device of the actuating housing 74 formed by the guide groove 85 and the transmission element 75.

Figure 16:
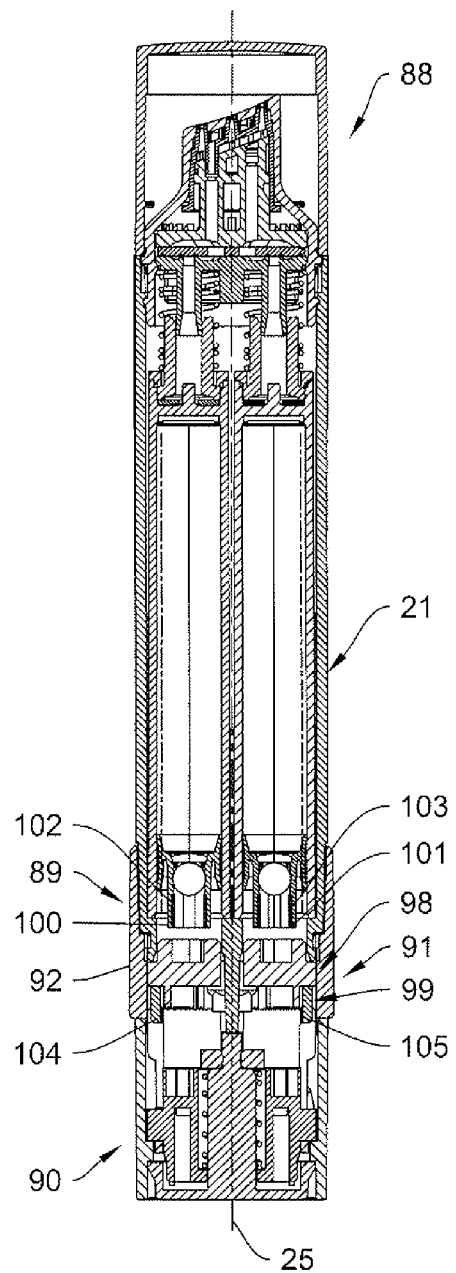

FIG. 16 shows a dispenser 88 which, analogous to the dispenser 20 shown in FIGS. 1 to 3, is furnished with a reservoir housing 21 that is provided with a setting device 89 and an actuation device 90. Together, the setting device 89 and the actuation device 90 form a manipulation device 91 and are disposed on a common longitudinal axis 25 with the reservoir housing 21.

Figure 17:
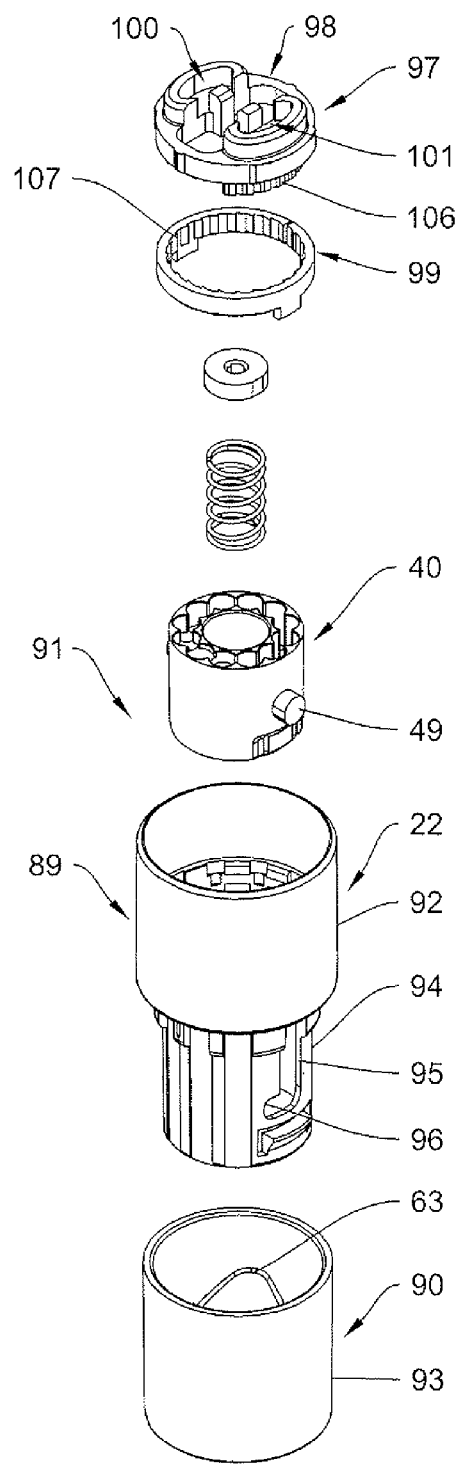
FIG. 17: illustrates an exploded view of the manipulation device of the dispenser shown in FIG. 16.

The manipulation device 91 is shown in an exploded view in FIG. 17 and comprises an adjusting housing 92 of the setting device 89 and an actuating housing 93 of the actuation device 90. A comparison with the manipulation device 22, illustrated in FIG. 5 of the dispenser 20, shows that the adjusting housing 92 is furnished with a guide section 94 which, in contrast to the guide section 44 of the adjusting housing 43, is provided with a guide slot 95, which at its lower end has a pin catch 96 that is designed here as a recession. The pin catch 96 interacts with the guide pin 49 of the transmission element 40, which is guided in the guide slot 95 so that when the actuating housing 93 of the actuation device 90 is rotated in a clockwise direction, the transmission element 40 is moved upward on the longitudinal axis 25 by the guide web 63. By contrast, when the actuating housing 93 is rotated in an anti-clockwise direction, a translational upward movement of the transmission element 40 is blocked on the longitudinal axis 25 as a result of the retention of the guide pin 49 in the pin catch 96. The guide slot 95 of the adjusting housing 92 formed in this manner thus defines a direction of actuation and rotation for the actuation device 90.

The manipulation device 91 of the dispenser 88 further differs from the manipulation device 22 of the dispenser 20 in that it features a modularly configured latching device 97 that has two latching elements 98, 99 of an annular design, which are formed independently from one another and which are arranged between the reservoir housing 21 and the adjusting housing 92, such that the latching element 98 is connected in a rotationally fixed manner to the reservoir housing 21 via surface recessions 100, 101, into which projections 102, 103 of the reservoir housing 21 come into engagement. The latching element 99 has pawl projections 104, 105 via which the latching element 99 is connected to the adjusting housing 92 in a rotationally fixed manner. A latching engagement is produced between the latching element 98 and the latching element 99 with the aid of a toothed pawl portion 106, 107, which is formed at the latching element 98 and at the latching element 99, and which enables a relative rotation of the latching elements 98, 99 in the embodiment shown in FIG. 17 with the aid of inclined tooth flanks 108 only in an anti-clockwise direction, such that, in the embodiment shown in FIGS. 16 and 17 of the dispenser 88, the actuation device 90 can be actuated in a clockwise direction and the setting device 89 can be actuated in an anti-clockwise direction.

Figures 18, 19:
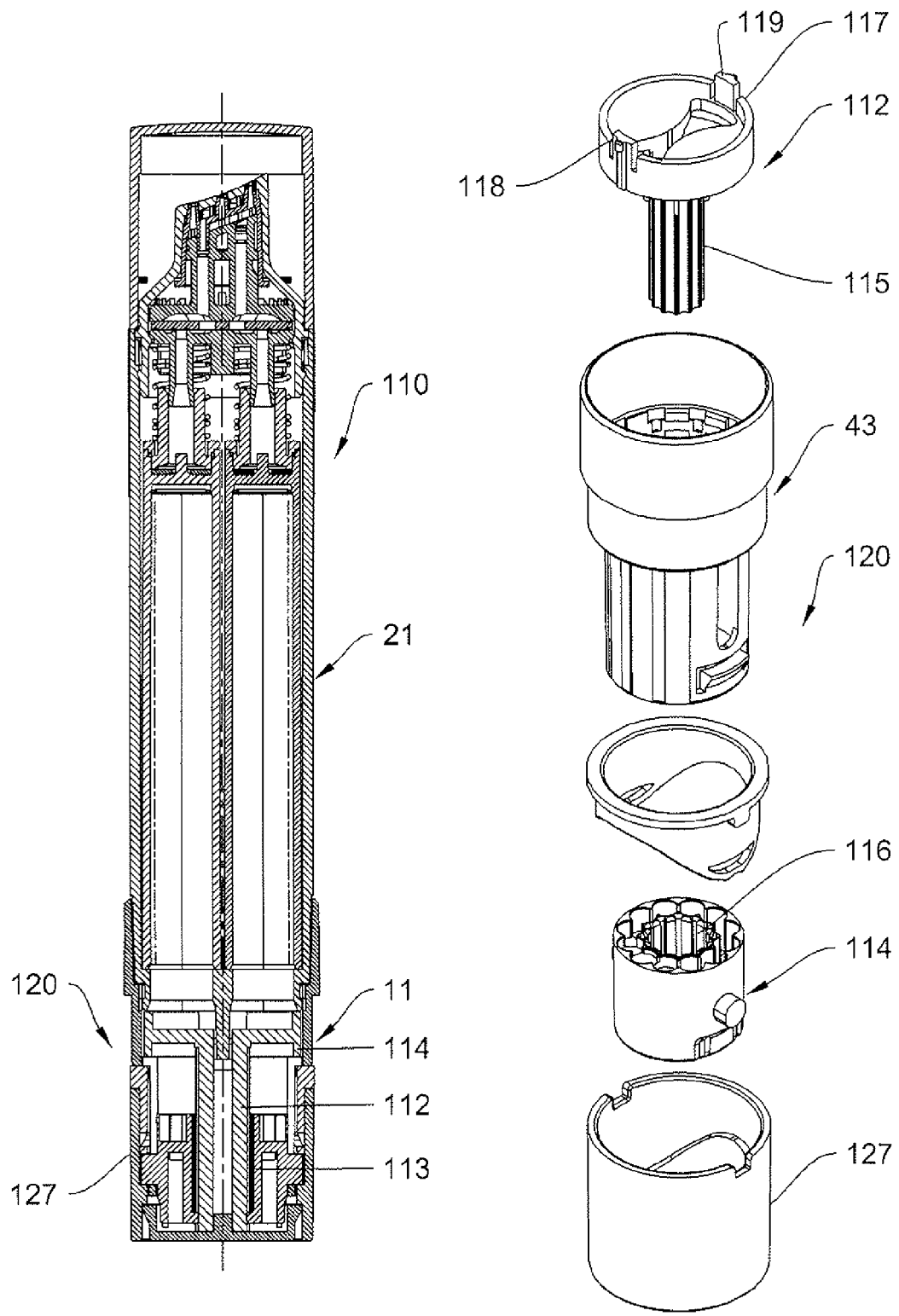
FIG. 18: illustrates another embodiment of a dispenser in a longitudinal cross-sectional view.
FIG. 19: illustrates an exploded view of the manipulation device of the dispenser shown in FIG. 18.

FIGS. 18 and 19, in another embodiment, show a dispenser 110 with a manipulation device 120 which, in contrast to the previously explained dispenser 88, features a latching device 111 that has a latching axle 112 that is connected to the reservoir housing 21 in a rotationally fixed manner and that engages with a hub designed as a latching sleeve 113 of a transmission element 114, thereby producing a latching engagement between a toothed latching portion 115 formed on the outer circumference of the latching axle 112 and a toothed latching portion 116 formed on the bore wall of the latching sleeve 113. The latching axle 112 is furnished with a disc-shaped axle base 117 which, at its upper edge, features projections 118, 119 for engagement with recessions (not shown here in greater detail) formed at the lower edge of the reservoir housing 21, and produces a rotationally fixed connection to the reservoir housing 21.

FIG. 21 shows a cross-sectional view of the manipulation device 120 illustrated in FIG. 20 having the latching axle 112 engaging with the latching sleeve 113 of the transmission element 114, wherein in the illustrated embodiment, the toothed latching portion 115 of the latching axle 112 in the cross-section features symmetrically designed latching teeth 121 that come into engagement with the toothed latching portion 116 of the transmission element 114 formed by the latching grooves 122. Due to the symmetrical design of the latching teeth 121, the latching engagement between the latching axle 112 and the latching sleeve 113 enables a relative rotation both in a clockwise direction and in an anti-clockwise direction. In contrast hereto, the latching axle 123 shown in FIG. 23 has a toothed latching portion 124 having latching teeth 125 that are designed in a pawl-like manner and with inclined tooth flanks 126, which enable a relative rotation between the adjusting housing 43 (FIG. 19) and the reservoir housing 21 (see FIG. 18), only in an anti-clockwise direction, by the latching grooves 122 of the toothed latching portion 116 of the transmission element 114.

FIGS. 24 to 26 illustrate another embodiment of a manipulation device 130 which, just like the manipulation devices 22, 42, 70, 91 and 120 already described before, can be combined with the reservoir housing 21, wherein, in contrast to the manipulation devices 22, 42, 70, 91 and 120 already described before, the manipulation device 130 has a guide section 132 that is formed independently of the adjusting housing 131 and that is formed as a guide housing and is connected in a rotationally fixed manner to the reservoir housing 21 via a fastening ring 133 formed at the upper end thereof by means of a latching connection 134. As is apparent in particular from a combined view of FIGS. 25 and 26, the guide section 132 is equipped with guide slots 135 in which a guide pin 136 of a pin arrangement is formed as a guide ring 137 so each is accommodated so as to be axially guided therein.

Furthermore, in particular, FIG. 25 shows that a latching engagement 138 is produced at the lower end of the guide section 132 between the guide section 132 and an actuating housing 139 of an actuation device 162 that is disposed on the guide section 132 so as to be rotatable. The actuating housing 139, at its inner wall 140, has a guide web 141 having a contact contour 142 that is formed with a defined gradient, such that when the actuating housing 139 is relatively rotated, the guide pins 136 slide along the contact contour 142 on the guide section 132 and, thereby, execute an axial movement in the guide slots 135 of the guide section 132. This axial movement is directed either upwardly or downwardly as a function of the direction of rotation of the actuating housing 139 and results in the guide ring 137 executing a corresponding upward or downward movement.

Provision is made for a helical spring 148 on a pin 144 that is formed at a bottom 143 of the guide section 132. The helical spring 148 is provided with one end thereof supported against a bottom 145 of a transmission element 146 received in the guide section 132, and with the other end thereof supported against a stop 147 arranged on the pin 144. The helical spring 148 thus provides for the transmission element 146 to abut against the guide ring 137, wherein a cup-shaped projection 149 of the transmission element 146 engages with a ring opening 150 of the guide ring 137 (FIG. 25). At the same time, the helical spring 148 ensures that the guide pins 136 of the guide ring 137, in a defined manner, rest on the contact contour irrespective of the guide ring 137 executing either an upward movement or a downward movement in the guide section 132.

As is particularly apparent from a combined view of FIGS. 26 and 27, in the manipulation device 130, a setting device 161, which serves for the defined setting and rotation of the transmission element 146 on the longitudinal axis 25 of the manipulation device 130, is composed of several parts and, in addition to the adjusting housing 131, is formed here with a ring shape or sleeve shape that comprises a setting sleeve 151, which is disposed concentrically with respect to the adjusting housing 131 inside the guide section 132. The setting sleeve 151 is equipped with a setting pin 152 that protrudes radially outwardly and penetrates through a setting groove that is formed in the guide section 132, and upon engagement with a guide pocket 155 formed on an inner wall 154 of the adjusting housing 131, produces a rotationally fixed connection with the adjusting housing 131, such that when the adjusting housing 131 is rotated about the longitudinal axis 25 of the manipulation device 130, the setting sleeve 151 is forced to rotate as well. In this manner, the radial travel path traveled by the setting pin 152 is limited by radial stops 156, 157, which are defined by the setting groove 153. As is apparent in particular from a combined view of FIGS. 25 and 27, the transmission element 146, on its inner wall, is equipped with a contact surface 159 that has contact ledges 170 in a ring segment 160, which are arranged in a longitudinal direction along the circumference in both directions so as to ascend starting from a low positioned central contact ledge 170 defining a central position.

As is shown in particular in FIG. 25, the transmission element 146, at its outer wall 172, has follower projections 173 engaging with follower receptacles 175 formed at an inner wall 174 of the setting sleeve 151. By means of this aspect, the transmission element 146 is axially displaceable within the adjusting housing 151 and is received in the setting sleeve 151 so as to be rotationally fixed with respect to the longitudinal axis 25 of the manipulation device 130, such that when the outer adjusting housing 131 is rotated about the longitudinal axis 25, the transmission element 146 executes a corresponding rotation about the longitudinal axis 25 as well.

For the purpose of the defined relative arrangement of the adjusting housing 131, the transmission element 146 and the guide section 132 are connected in a rotationally fixed manner to the reservoir housing 21. A latching device 171 shown in FIG. 28 is provided between the adjusting housing 151 and the guide section 132, such that a latching nose 176 formed at the outer wall of the setting sleeve 151 interacts with a plurality of latching catches 178 that are formed along the circumference in the inner wall of the guide section 132, wherein by overcoming a rotational resistance, which determines a defined indexed position, a change can be made between the setting sleeve 151 and the guide section 132 from a defined rotational position, in which the latching nose 176 engages with a first latching catch 178, into another defined rotational position, in which the latching nose 176 engages with another (second) latching catch 178.

Due to the advantageous guiding and accommodation of the transmission element 146 in the guide ring 137, during the axial displacement of the guide ring 137 within the guide section 132 in response to a rotation of the actuating housing 139 with respect to the guide section 132 that is arranged at the reservoir housing 139 in a rotationally fixed manner, a torque is not transmitted to the transmission element 146. Consequently, a torque of the transmission element 146 cannot act on the plungers 38, 39 of the pumping devices 34, 35, for instance shown in FIG. 2, which may give rise to component failure of the plungers 38, 39.

| List of Reference Numerals | |
|---|---|
| 20 | Dispenser |
| 21 | Reservoir housing |
| 22 | Manipulation device |
| 23 | Setting device |
| 24 | Actuation device |
| 25 | Longitudinal axis |
| 26 | Reservoir |
| 27 | Reservoir |
| 28 | Valve device |
| 29 | Valve device |
| 30 | Mixing device |
| 31 | Output device |
| 32 | Applicator surface |
| 33 | Applicator cap |
| 34 | Pumping device |
| 35 | Pumping device |
| 36 | Pumping piston |
| 37 | Pumping piston |
| 38 | Plunger |
| 39 | Plunger |
| 40 | Transmission element |
| 41 | Latching device |
| 42 | Manipulation device |
| 43 | Adjusting housing |
| 44 | Guide section |
| 45 | Contact surface |
| 46 | Contact ledge |
| 47 | Bottom |
| 48 | Blind bore |
| 49 | Guide pin |
| 50 | Guide slot |
| 51 | Inner wall |
| 52 | Latching edge |
| 53 | Inner wall |
| 54 | Actuating housing |
| 55 | Latching web |
| 56 | Latching connection |
| 57 | Bearing sleeve |
| 58 | Pin |
| 59 | Stop |
| 60 | Bottom |

-continued

| List of Reference Numerals | |
|---|---|
| 61 | Helical spring |
| 62 | Central contact surface plane |
| 63 | Guide web |
| 64 | Contact contour |
| 65 | Indentation |
| 66 | Upwards ramp |
| 67 | Ramp vertex |
| 68 | Upwards ramp |
| 69 | Indentation |
| 70 | Manipulation device |
| 71 | Setting device |
| 72 | Actuation device |
| 73 | Adjusting housing |
| 74 | Actuating housing |
| 75 | Transmission element |
| 76 | Guide section |
| 77 | Bottom |
| 78 | Latching pin |
| 79 | Latching nose |
| 80 | Latching device |
| 81 | Opening edge |
| 82 | Opening |
| 83 | Inner wall |
| 84 | Guide section |
| 85 | Guide groove |
| 86 | Groove edge |
| 87 | Groove edge |
| 88 | Dispenser |
| 89 | Setting device |
| 90 | Actuation device |
| 91 | Manipulation device |
| 92 | Adjusting housing |
| 93 | Actuating housing |
| 94 | Guide section |
| 95 | Guide slot |
| 96 | Pin catch |
| 97 | Latching device |
| 98 | Latching element |
| 99 | Latching element |
| 100 | Surface recess |
| 101 | Surface recess |
| 102 | Projection |
| 103 | Projection |
| 104 | Pawl projection |
| 105 | Pawl projection |
| 106 | Toothed pawl portion |
| 107 | Toothed pawl portion |
| 108 | Toothed flank |
| 109 | |
| 110 | Dispenser |
| 111 | Latching device |
| 112 | Latching axle |
| 113 | Latching sleeve |
| 114 | Transmission element |
| 115 | Toothed latching portion |
| 116 | Toothed latching portion |
| 117 | Axle base |
| 118 | Projection |
| 119 | Projection |
| 120 | Manipulation device |
| 121 | Latching tooth |
| 122 | Latching groove |
| 123 | Latching axle |
| 124 | Toothed latching portion |
| 125 | Latching tooth |
| 126 | Tooth flank |
| 127 | |
| 128 | |
| 129 | |
| 130 | Manipulation device |
| 131 | Adjusting housing |
| 132 | Guide section |
| 133 | Fastening ring |
| 134 | Latching connection |
| 135 | Guide slot |
| 136 | Guide pin |
| 137 | Guide ring |

-continued

List of Reference Numerals

| | |
|---|---|
| 138 | Latching connection |
| 139 | Actuating housing |
| 140 | Inner wall |
| 141 | Guide web |
| 142 | Contact contour |
| 143 | Bottom |
| 144 | Pin |
| 145 | Bottom |
| 146 | Transmission element |
| 147 | Stop |
| 148 | Helical spring |
| 149 | Projection |
| 150 | Ring opening |
| 151 | Setting sleeve |
| 152 | Setting pin |
| 153 | Setting groove |
| 154 | Inner wall |
| 155 | Guide pocket |
| 156 | Stop |
| 157 | Stop |
| 158 | Inner wall |
| 159 | Contact surface |
| 160 | Ring segment |
| 161 | Setting device |
| 162 | Actuation device |
| 163 | |
| 164 | |
| 165 | |
| 166 | |
| 167 | |
| 168 | |
| 169 | |
| 170 | Contact ledge |
| 171 | Latching device |
| 172 | Outer wall |
| 173 | Follower projection |
| 174 | Inner wall |
| 175 | Follower receptacle |
| 176 | Latching nose |
| 177 | Inner wall |
| 178 | Latching catch |

The invention claimed is:

1. A dispenser for dosed dispensing of at least two components received in a plurality of reservoirs, wherein the dispenser comprises:
   (a) a plurality of pumping devices, wherein a separate pumping device is assigned to each reservoir of the plurality of reservoirs, wherein the pumping devices are provided with an actuation device for axial displacement of plungers acting on pumping pistons of the pumping devices in order to dispense the at least two components from an output device connected to the plurality of reservoirs; and
   (b) a dosing device, wherein the actuation device acts on the plungers indirectly via the dosing device, and the dosing device is provided with a setting device that is actuatable to change a position of a transmission element acting on the plungers for setting a quantity ratio of the at least two components, wherein the setting device is rotated in order to set the quantity ratio of the at least two components, and the actuation device is rotated as well in order to axially displace the plungers of the pumping device.

2. A dispenser according to claim 1, wherein the setting device of the dosing device has an adjusting housing that is rotatable about a longitudinal axis of a reservoir housing of the dispenser, wherein the plurality of reservoirs for receiving the at least two components and the pumping devices are received in the reservoir housing, and the transmission element is disposed in the reservoir housing so as to be rotationally fixed with respect to the adjusting housing and so as to be axially displaceable on a longitudinal axis of the adjusting housing for actuating the plurality of pumping devices, wherein the transmission element comprises a contact surface of an annular configuration or that is formed as a ring segment having a surface contour changing in shape along a circumference and that interacts with pumping pistons of the plurality of pumping devices.

3. A dispenser according to claim 2, wherein the actuation device for dispensing the at least two components has an actuating housing that is rotatable about the longitudinal axis of the dispenser relative to the adjusting housing, wherein the actuating housing is equipped with a guide arrangement that enables axial displacement of the transmission element, wherein a first guide device of the guide arrangement is formed in the actuating housing and interacts with a second guide device of the guide arrangement, wherein the second guide device is formed independently of the actuating housing, for converting a rotary movement of the actuating housing into an axial movement of the transmission element.

4. A dispenser according to claim 3, wherein the second guide device has a guide section having an axially oriented guide slot and a pin arrangement positioned at the transmission element with at least one radial guide pin that penetrates through the guide slot and a contact end of the at least one radial guide pin interacts with the first guide device of the actuating housing.

5. A dispenser according to claim 4, wherein the actuating housing, for the purpose of forming the first guide device, has a guide path on an inner wall that is coaxially disposed with respect to the guide section, wherein the guide path has a contact contour interacting with the contact end of the at least one radial guide pin and controlling the axial movement of the transmission element.

6. A dispenser according to claim 5, wherein the axially oriented guide slot is formed in the guide section, and at a lower end thereof, the axially oriented guide slot comprises a pin catch for accommodating the at least one radial guide pin to define a direction of rotation of the actuation device.

7. A dispenser according to claim 4, wherein, in order to define an initial position of the actuation device, in which the plurality of pumping devices are not acted upon by the transmission element, a spring device is disposed between a stop formed at the guide section and the transmission element.

8. A dispenser according to claim 7, wherein the stop is formed at an axial end of a second pin formed at a bottom of the guide section and extending through an opening formed in a bottom of a central cup-shaped indentation of the transmission element, wherein the spring device is configured in the form of a helical spring disposed in an annular space formed between the second pin and the indentation and that extends between the stop and the bottom of the central cup-shaped indentation of the transmission element.

9. A dispenser according to claim 4, wherein, for the purpose of defining an initial position of the actuation device, in which the plurality of pumping devices are not acted upon by the transmission element, a latching device is disposed at an axial end of a latching pin that is arranged in the guide section, and the transmission element is disposed in the initial position in the latching device so that the latching device engages behind an edge of a central opening in the transmission element.

10. A dispenser according to claim 5, wherein the guide path disposed on the inner wall of the actuating housing comprises a guide groove, wherein groove edges of the guide groove run in parallel to one another and the at least one guide pin is received between the groove edges of the guide groove.

11. A dispenser according to claim 4, wherein the second guide device is formed by the guide section, wherein the guide section is formed by the adjusting housing and the pin arrangement with the at least one guide pin formed at the transmission element, so that when the adjusting housing is rotated the transmission element is correspondingly rotated as well.

12. A dispenser according to claim 2, wherein, in order to define a relative arrangement of the adjusting housing with respect to the reservoir housing, a latching device is disposed between the adjusting housing and the reservoir housing, and has a plurality of indexed positions for a defined assignment of contact regions of the transmission element formed on the contact surface, and a plurality of plungers act on the pumping pistons of the plurality of pumping devices.

13. A dispenser according to claim 12, wherein the latching device comprises a modular latching unit that is insertable between the reservoir housing and the adjusting housing, and the modular latching unit is actuatable as a function of a direction of rotation with respect to the reservoir housing to enable a relative rotation of the adjusting housing.

14. A dispenser according to claim 13, wherein the latching unit comprises
    i. a first latching element of an annular construction that is connectable to the reservoir housing in a rotationally fixed manner; and
    ii. a second latching element of an annular construction that is connectable to the adjusting housing in a rotationally fixed manner, wherein the first latching element and the second latching element interact with one another via a latching engagement that is provided in a common annular plane with the aid of a plurality of latching projections, wherein the plurality of latching projections are formed by a toothed pawl section.

15. A dispenser according to claim 14, wherein one of the first latching element and the second latching element comprises the toothed pawl section, only in a ring segment.

16. A dispenser according to claim 12, wherein the latching device further comprises a latching axle that is connected to the reservoir housing and that engages with a hub of the transmission element that is constructed as a latching sleeve to produce a latching engagement.

17. A dispenser according to claim 16, wherein first latching projections formed on a circumference of the latching axle interact with second latching projections formed on a bore wall of the latching sleeve to produce the latching engagement.

18. A dispenser according to claim 17, wherein the latching projections of the latching axle are formed by a toothed latching portion.

19. A dispenser according to claim 4, wherein the axially oriented guide slot is formed in the guide section, and at a lower end thereof, the axially oriented guide slot comprises a pin catch for accommodating the at least one radial guide pin to define a direction of rotation of the actuation device.

20. A dispenser according to claim 12, wherein the contact regions are formed on the contact surface of the transmission element by contact ledges that are arranged in a stepped sequence.

21. A dispenser according to claim 20, wherein the contact ledges are formed by blind bores that are arranged in a horizontal surface of the transmission element.

22. A dispenser for dosed dispensing of at least two components received in a plurality of reservoirs, wherein the dispenser comprises:
    (a) a plurality of pumping devices, wherein a separate pumping device is assigned to each reservoir of the plurality of reservoirs, wherein the pumping devices are provided with an actuation device for axial displacement of plungers acting on pumping pistons of the pumping devices in order to dispense the at least two components from an output device connected to the plurality of reservoirs; and
    (b) a dosing device, wherein the actuation device acts on the plungers indirectly via the dosing device, and the dosing device is provided with a setting device that is actuatable to change a position of a transmission element acting on the plungers for setting a quantity ratio of the at least two components, wherein the setting device is rotated in order to set the quantity ratio of the at least two components, and the actuation device is rotated as well in order to axially displace the plungers of the pumping device,
    wherein the setting device of the dosing device has an adjusting housing that is rotatable about a longitudinal axis of a reservoir housing of the dispenser, wherein the plurality of reservoirs for receiving the at least two components and the pumping devices are received in the reservoir housing, and the transmission element is disposed in the reservoir housing so as to be rotationally fixed with respect to the adjusting housing and so as to be axially displaceable on a longitudinal axis of the adjusting housing for actuating the plurality of pumping devices, wherein the transmission element comprises a contact surface of an annular configuration or that is formed as a ring segment having a surface contour changing in shape along a circumference and that interacts with the pumping pistons of the plurality of pumping devices,
    wherein the actuation device for dispensing the at least two components has an actuating housing that is rotatable about the longitudinal axis of the dispenser relative to the adjusting housing, wherein the actuating housing is equipped with a guide arrangement that enables axial displacement of the transmission element, wherein a first guide device of the guide arrangement is formed in the actuating housing and interacts with a second guide device of the guide arrangement, wherein the second guide device is formed independently of the actuating housing, for converting a rotary movement of the actuating housing into an axial movement of the transmission element,
    wherein the second guide device has a guide section having an axially oriented guide slot and a pin arrangement positioned at the transmission element with at least one radial guide pin that penetrates through the guide slot and a contact end of the at least one radial guide pin interacts with the first guide device of the actuating housing, and
    wherein, for forming the second guide device, the guide section is connected to the reservoir housing in a rotationally fixed manner, and the pin arrangement comprises a guide ring having the at least one guide pin, and the transmission element is received in the guide ring so as to be rotatable and is connected to the adjusting housing in a rotationally fixed manner by a radial engagement device so that when the adjusting housing is rotated, a relative rotation of the adjusting housing is effected with respect to the guide section.

23. A dispenser according to claim claim 22, wherein the radial engagement device comprises a setting sleeve in which the transmission element is received in a rotationally fixed manner and so as to be axially displaceable, wherein the setting sleeve produces an engaging connection with the adjusting housing via a setting pin that penetrates radially through the guide section in a setting groove.

24. A dispenser according to claim 23, wherein, for the purpose of the defined relative arrangement of the adjusting housing, a latching device is disposed between the setting sleeve and the guide section, and the latching device has a plurality of indexed positions for a defined assignment of contact regions of the transmission element formed on the contact surface, and a plurality of plungers act on the plurality of pumping devices.

* * * * *